United States Patent
Breslich et al.

(12) 
(10) Patent No.: US 12,369,907 B2
(45) Date of Patent: Jul. 29, 2025

(54) CANNULATED TISSUE NEEDLE WITH SUTURE GRASPING MECHANISM

(71) Applicant: Conmed Corporation, Utica, NY (US)

(72) Inventors: Grady Breslich, St. Petersburg, FL (US); Peter Miller, Largo, FL (US)

(73) Assignee: Conmed Corporation, Utica, NY (US)

( * ) Notice: Subject to any disclaimer, the term of this patent is extended or adjusted under 35 U.S.C. 154(b) by 0 days.

(21) Appl. No.: 17/029,617

(22) Filed: Sep. 23, 2020

(65) Prior Publication Data

US 2021/0085311 A1   Mar. 25, 2021

Related U.S. Application Data

(60) Provisional application No. 62/904,819, filed on Sep. 24, 2019.

(51) Int. Cl.
*A61B 17/04* (2006.01)
*A61B 17/00* (2006.01)

(52) U.S. Cl.
CPC ...... *A61B 17/0485* (2013.01); *A61B 17/0483* (2013.01); *A61B 2017/00738* (2013.01)

(58) Field of Classification Search
CPC ............ A61B 17/0485; A61B 17/0483; A61B 2017/00738; A61B 2017/0445
See application file for complete search history.

(56) References Cited

U.S. PATENT DOCUMENTS

| | | | |
|---|---|---|---|
| 8,808,313 B2 * | 8/2014 | Thorne | A61B 17/0485 606/145 |
| 2012/0209300 A1 * | 8/2012 | Torrie | A61B 17/0485 606/148 |
| 2014/0012292 A1 * | 1/2014 | Stewart | A61B 17/0469 606/148 |

FOREIGN PATENT DOCUMENTS

WO   2019/118835   6/2019

OTHER PUBLICATIONS

Conmed Corporation, Shoulder Restoration System, Barber et al. Arthroscopy, 2012, Agrawal V. Int J Shoulder Surg, 2012, pp. 1-20.

* cited by examiner

*Primary Examiner* — Katherine M Shi
*Assistant Examiner* — Mohammed S Adam

(57) ABSTRACT

A suture passer for use in arthroscopic soft tissue repair procedures. The suture passer includes a cannulated needle having a distal tip. A post is slidable within the cannulated needle. A snare is slidable within the cannulated needle between an extended position and a retracted position. In the extended position, the snare extends from the distal tip of the cannulated needle and in the retracted position, the snare extends around the post. The suture passer may have a handle extending proximally from the cannulated needle. In use, suture is passed through an open region between the snare and the post in the extended position. As the snare and, in some cases, the post, are retracted, the snare extends around the post and closes the open region, trapping the suture between the snare and the post in a closed region.

19 Claims, 7 Drawing Sheets

CANNULATED TISSUE NEEDLE WITH SUTURE GRASPING MECHANISM

CROSS-REFERENCE TO RELATED APPLICATION

The present application claims priority to and the benefit of U.S. Provisional Patent Application No. 62/904,819, filed on Sep. 24, 2019 and entitled "Cannulated Tissue Needle with Suture Grasping Mechanism," the entirety of which is incorporated herein by reference.

BACKGROUND OF THE INVENTION

1. Field of the Invention

The present invention relates to a suture passer and, more particularly, to a suture passer for arthroscopic soft tissue repair procedures.

2. Description of Related Art

An exemplary arthroscopic soft tissue repair procedure is a Bankart repair. The Bankart repair is a surgical repair of shoulder instability to prevent recurring shoulder dislocations. In this procedure, sutures are passed through the tissue using an instrument and the sutures are anchored to the bone to allow the tissue to heal to the bone. Existing instruments, such as the ConMed Spectrum and Spectrum II suture passers, employ a cannulated needle to pierce the tissue. Then, a filament of material, with or without eyelets, is passed down the cannulated needle into the joint space and out an adjacent portal. The suture to be passed through the tissue is then attached to the filament. The filament is then pulled out of the tissue, pulling the fixation suture into the tissue.

Other instruments, such as the ConMed Blitz Suture Passer, are designed to eliminate the step of shuttling the fixation suture by deploying a loop of material out of the cannulated needle. Once the needle is passed through the tissue, the loop is deployed into the joint out the cannulation of the needle. The fixation suture is then passed into the loop, the loop and suture are retracted into the cannulated needle, and the cannulated needle is removed from the tissue, pulling the fixation suture through the tissue. These devices require a separate instrument to place the suture into the loop.

Attempting to improve upon the above two methods, instruments such as the Mitek Ideal Pass, employ a cannulated needle with a hood disposed in the cannulation. In use, the cannulated needle is passed through the tissue, the hook is deployed from the cannulation, the suture is introduced into the hook, the hook is retracted with the suture, and the needle is removed from the tissue, pulling the fixation suture through the tissue. These instruments, with a hood disposed within the cannulation, require a larger diameter cannulation and needle than the two devices described above.

Therefore, there exists a need for a cannulated tissue needle with an integrated suture grasping mechanism that allows for suture to be grasped and pulled through the tissue while minimizing the size of cannulation and needle.

The term "suture" as used herein may be any type of filamentous material such as a biocompatible or bioabsorbable filament, ribbon, tape, woven or non-woven material.

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

BRIEF SUMMARY OF THE INVENTION

Embodiments of the present invention are directed to a suture passer. The suture passer includes a cannulated needle having a distal tip. A post is slidable within the cannulated needle. A snare is slidable within the cannulated needle between an extended position and a retracted position. In the extended position, the snare extends from the distal tip of the cannulated needle and in the retracted position, the snare extends around the post.

Another embodiment of the suture passer includes a proximal handle with a cannulated needle extending distally therefrom. The cannulated needle terminates in a distal tip. The suture passer additionally includes a post slidable within the cannulated needle between an extended position and a retracted position and a snare slidable within the cannulated needle between an extended position and a retracted position. In the extended position, the snare extends from the distal tip of the cannulated needle and in the retracted position, the snare extends around the post.

According to another aspect, the present invention is a method for passing suture. The method includes the steps of: (i) providing a suture passer having a cannulated needle with a distal tip, a post slidable within the cannulated needle, and a snare slidable within the cannulated needle; (ii) passing the distal tip of the cannulated needle through a tissue; (iii) extending the snare and the post out from the distal tip of the cannulated needle to an extended position, forming an open region between the snare and the post; (iv) passing suture through the open region between the snare and the post; and (v) retracting the snare proximally through the cannulated needle to a retracted position, closing the open region around the suture.

These and other aspects of the invention will be apparent from and elucidated with reference to the embodiment(s) described hereinafter.

BRIEF DESCRIPTION OF THE SEVERAL VIEWS OF THE DRAWING(S)

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments. Reference is now made briefly to the accompanying drawings, in which.

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
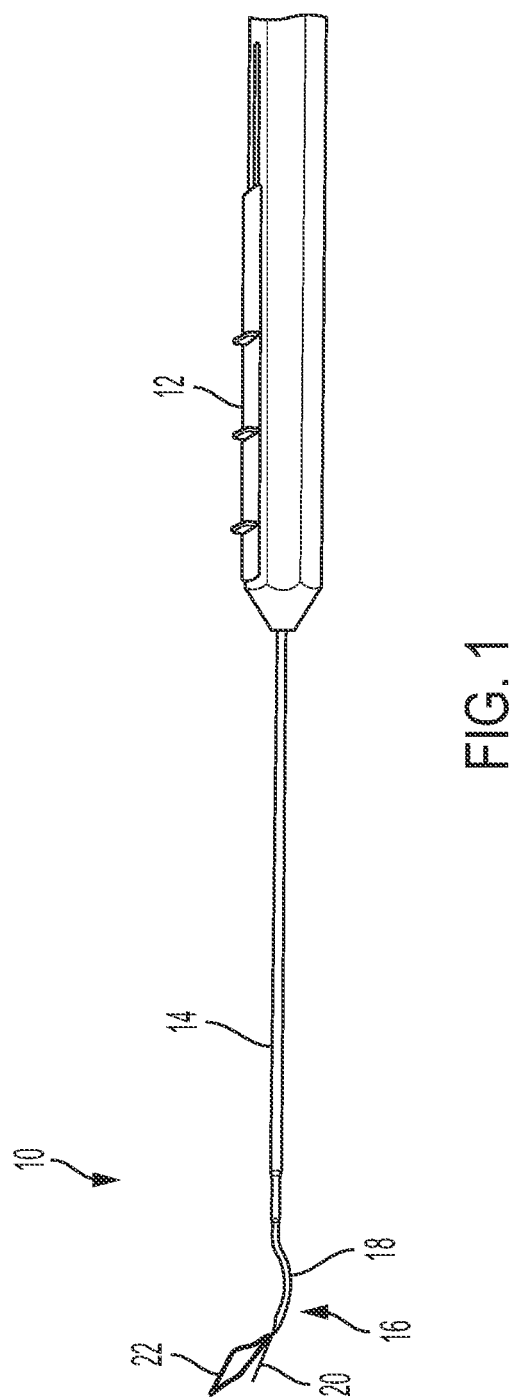
FIG. 1 is a side view of a suture passer, according to an embodiment.

Referring now to the figures, wherein like reference numerals refer to like parts throughout, FIG. 1 shows a side view of a suture passer 10, according to an embodiment. The suture passer 10 comprises a proximal handle 12 with a cannulated needle 14 extending distally therefrom. The cannulated needle 14 terminates in a distal tip 16. In the depicted embodiment, the cannulated needle 14 has a bent portion 18. The bent portion 18 in the cannulated needle 14 in FIG. 1 is at the distal tip 16. The bent portion 18 may comprise a bend or curve of a variety of configurations. For example, the bent portion 18 may be a crescent shape, as shown in the Figures, or a 45-degree curve.

As mentioned above, the needle 14 is cannulated such that elements or features may move therein. In FIG. 1, the cannulated needle 14 has a post 20 slidable therein. The post 20 moves proximally and distally within the cannulated needle 14 and may have various bend configurations to assist in suture manipulation. The post 20 may have any of the bend configurations of the cannulated needle 14 as recited above or any other conceivable bend configurations.

Still referring to FIG. 1, the suture passer 10 additionally includes a snare 22. The snare 22 is a loop of super-elastic nitinol or any other similar material. The shape of the snare 22 allows the snare 22 to be deflected away from the post 20 when deployed (in an extended position) and capture the post 20 when retracted (in a fully retracted position). In the depicted embodiment, the snare 22 is diamond shaped in the extended position. In use, the post 20 and the snare 22 begin fully retracted within the cannulated needle 14. Specifically, according to an embodiment, in the fully retracted position, the post 20 and the snare 22 do not extend out from the distal tip 16 of the cannulated needle 14.

Figure 2:
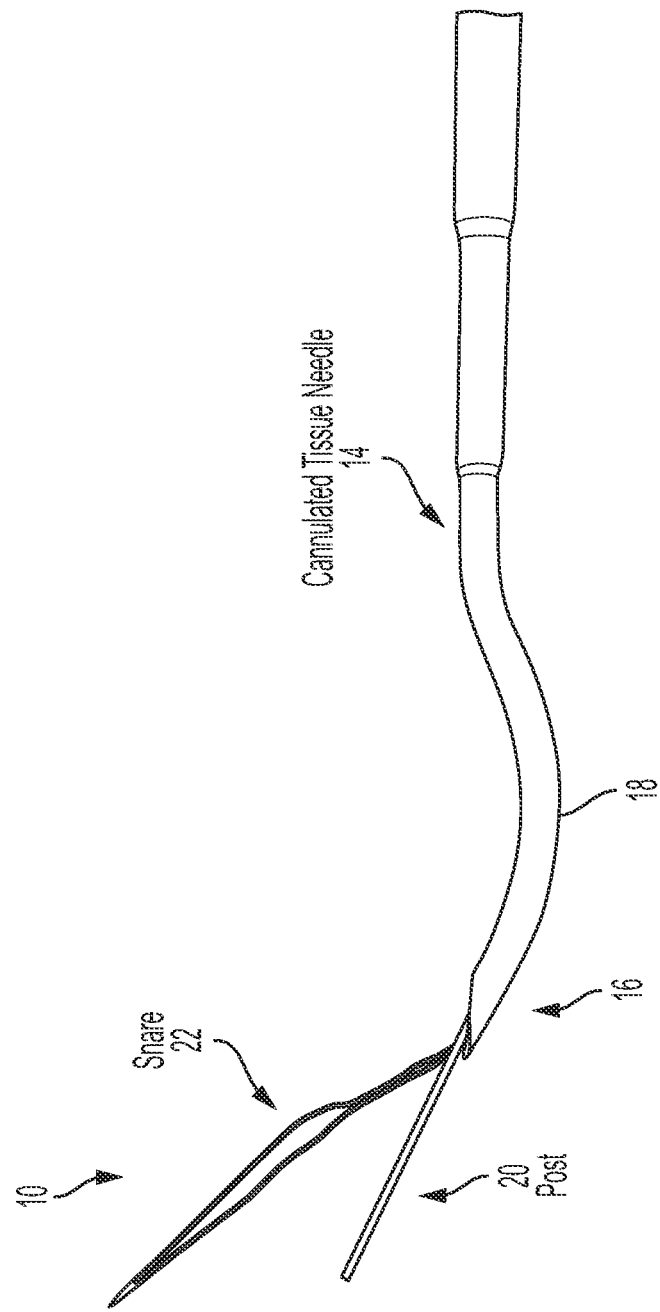
FIG. 2 is a close-up, side view of a distal tip of the suture passer in an extended position, according to an embodiment.

With the post 20 and the snare 22 in the fully retracted position, the distal tip 16 of the cannulated needle 14 is used to pierce through tissue at the surgical site. After piercing through the tissue, the post 20 and the snare 22 are deployed out from the distal tip 16 of the cannulated needle 14 to the extended position. FIG. 2 shows a close-up, side view of the distal tip 16 of the suture passer 10 in the extended position, according to an embodiment. As shown in FIG. 2, in the extended position, the post 20 and the snare 22 extend distally from the distal tip 16 of the cannulated needle 14.

Still referring to FIG. 2, the snare 22 has a shape such that when it is in the extended position, fully extended out from the distal tip 16 of the cannulated needle 14, it bends away from the post 20 to create an open region 24 sized and configured to receive suture 26. As shown in FIG. 2, in the extended position, the snare 22 extends at an angle relative to the post 20. The snare 22 extends at an angle relative to the post 20, exposing the open region 24 therebetween.

Figure 3:
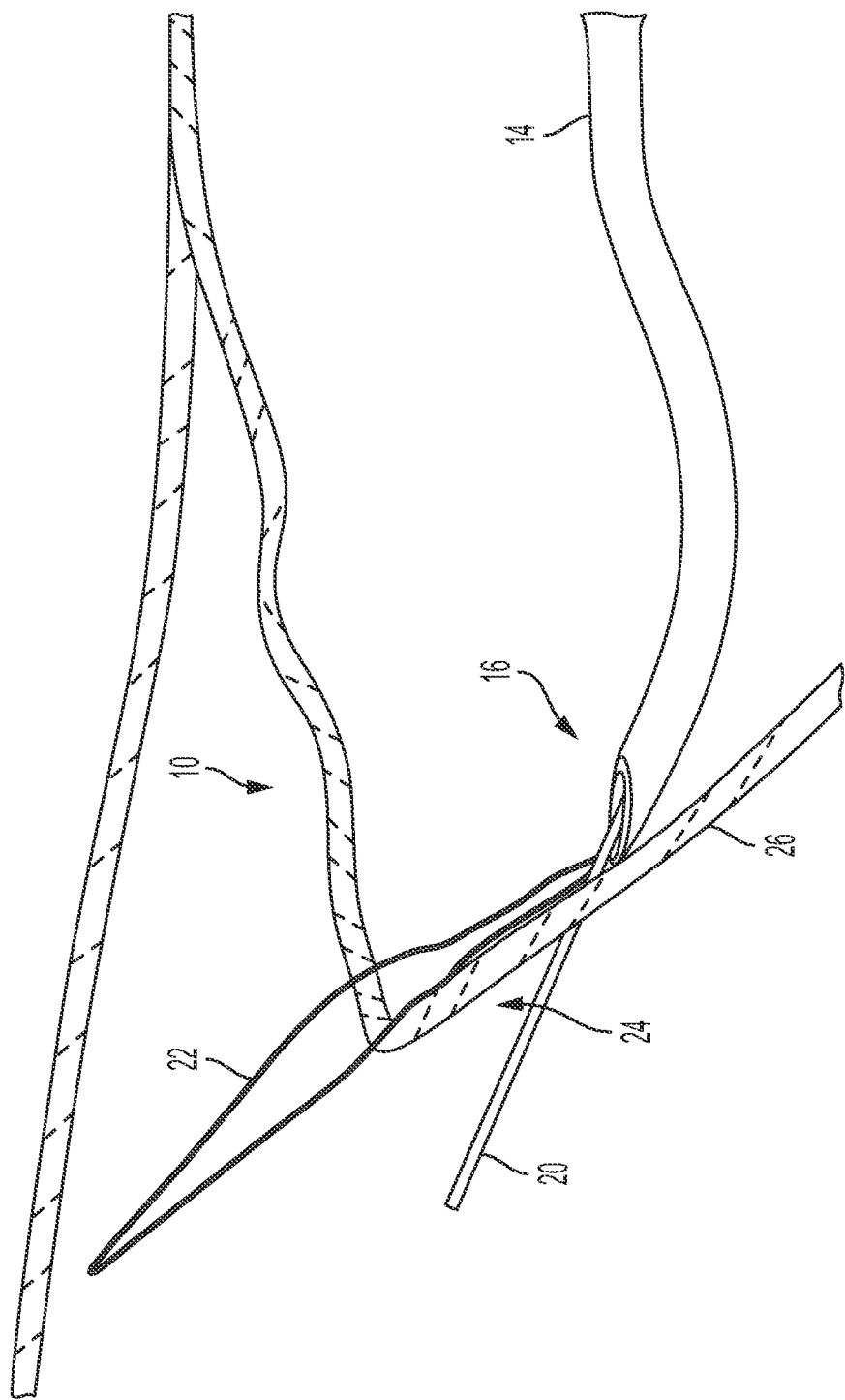
FIG. 3 is a close-up, side view of suture extending through an open Region between the snare and the post of the suture passer, according to an embodiment.

Turning now to FIG. 3, there is shown a close-up, side view of suture 26 extending through the open region 24 between the snare 22 and the post 20 of the suture passer 10, according to an embodiment. After the cannulated needle 14 is used to pierce through the tissue at the surgical site and the post 20 and the snare 22 are in the extended position, suture 26 can be positioned through the open region 24 between the post 20 and the snare 22, as shown in FIG. 3.

Figure 4:
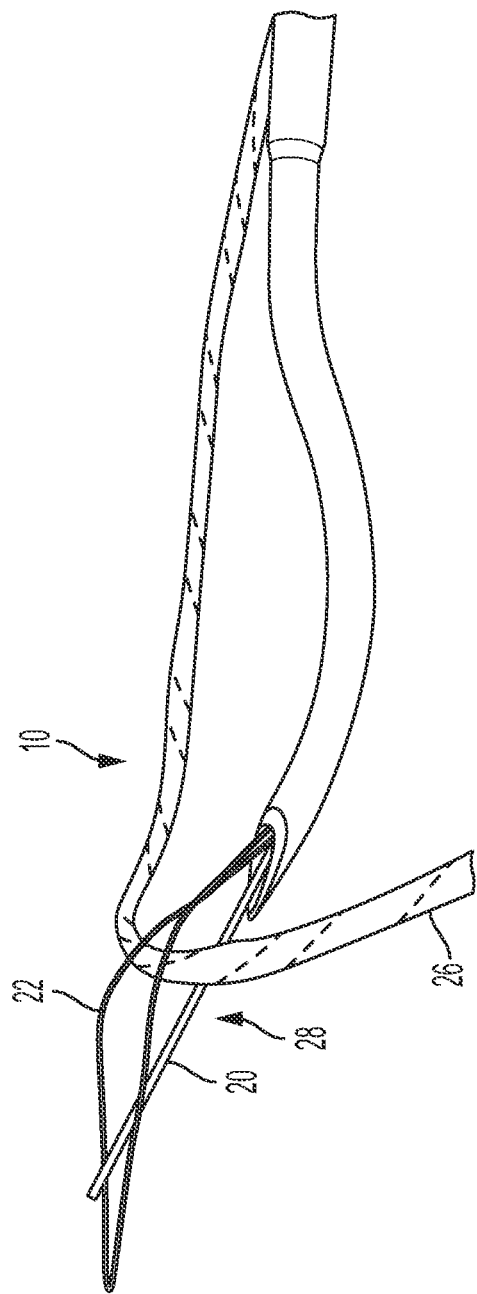
FIG. 4 is a close-up, side view of the snare of the suture passer in a first partially retracted position, according to an embodiment.
Figure 5:
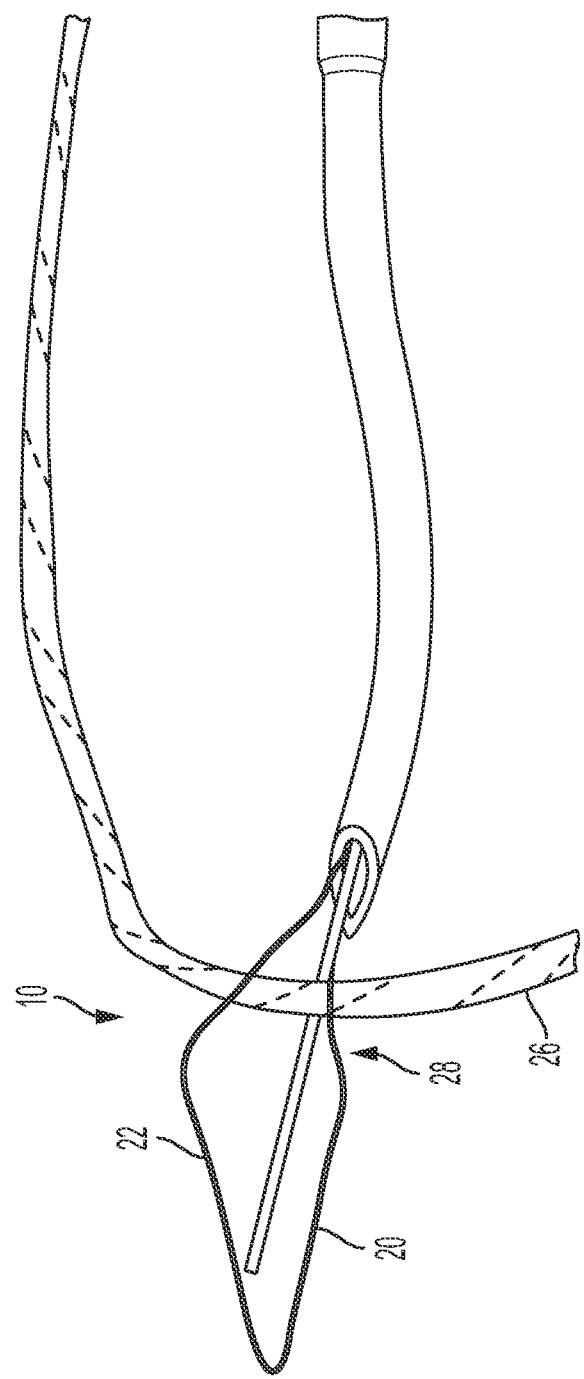
FIG. 5 is a close-up, top view of the snare of the suture passer in the first partially retracted position, according to an embodiment.

Referring now to FIGS. 4 and 5, there are shown close-up, side and top views of the snare 22 of the suture passer 10 in a first partially retracted position, according to an embodiment. With the suture 26 in the open region 24 (FIG. 3), the snare 22 is partially retracted to a first partially retracted position, enclosing the open region 24 such that a closed region 28 is created surrounding the suture 26. As shown in FIGS. 4 and 5, the suture 26 extends through the closed region 28 and the post 20 extends through the snare 22 when the suture passer 10 is in first partially retracted position. Again, the shape of the snare 22 allows it to capture the post 20 to create the closed region 28 around the suture 26.

Figure 6:
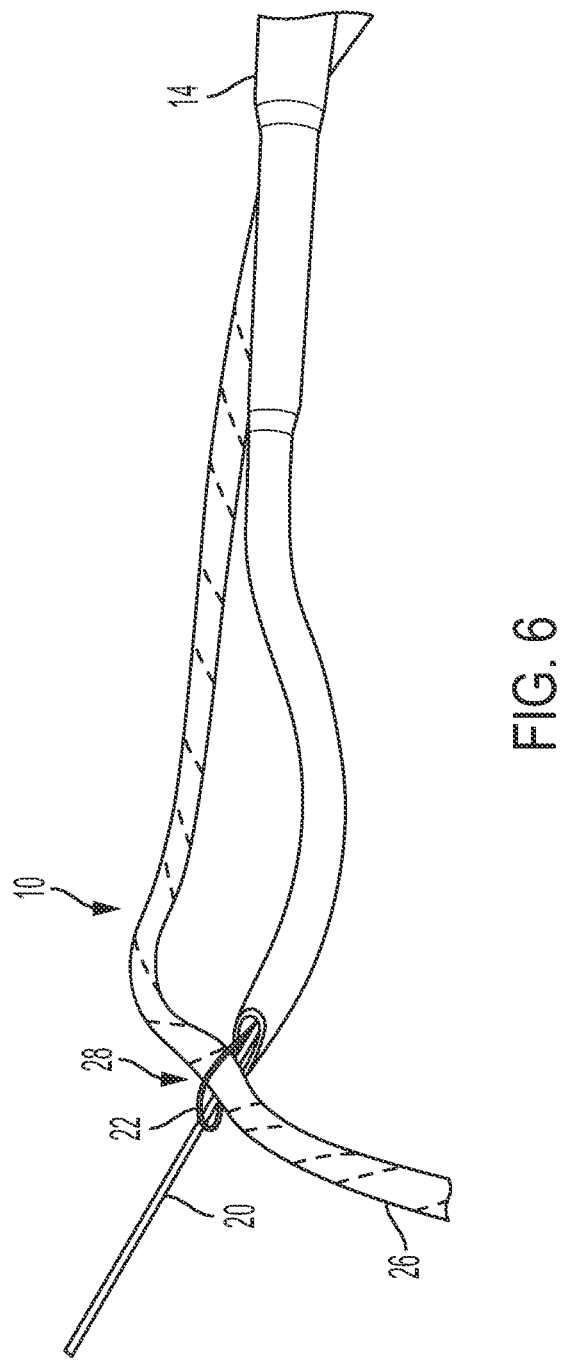
FIG. 6 is a close-up, perspective view of the snare of the suture passer in second partially retracted position, according to an embodiment.

Turning now to FIG. 6, there is shown a close-up, perspective view of the snare 22 of the suture passer 10 in a second partially retracted position, according to an embodiment. From the first partially retracted position in FIG. 5, the snare 22 is further retracted. The additional retraction of the snare 22 causes the closed region 28 to shrink. In other words, the size of the closed region 28 decreases when the snare 22 is retracted from the first partially retracted position to the second partially retracted position. As shown in FIG. 6, the post 20 substantially maintains its positioning among the extended position and first and second partially retracted positions. In an alternative embodiment, the post 20 may be partially retracted within the cannulated needle 14 at the first and/or second partially retracted positions.

Figure 7:
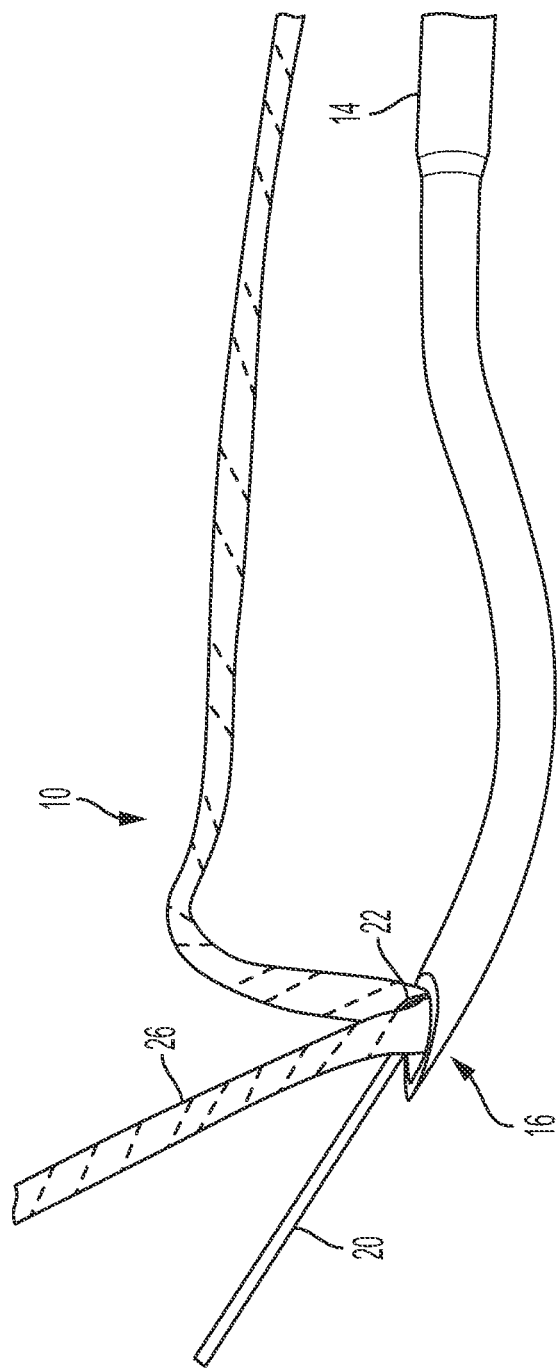
FIG. 7 is a close-up, side view of the snare of the suture passer in the fully retracted position, according to an embodiment.

Referring now to FIG. 7, there is shown a close-up, side view of the snare 22 of the suture passer 10 in the fully retracted position, according to an embodiment. From the second partially retracted position in FIG. 6, the snare 22 is further retracted until it reaches the fully retracted position in FIG. 7. An exemplary embodiment of the suture passer 10 in the fully retracted position is shown in FIG. 7. In the fully retracted position in FIG. 7, the snare 22 holds the suture 26 tightly against the post 20 at the distal tip 16 of the cannulated needle 14. In an embodiment, the post 20 may be fully retracted within the cannulated needle 14 at the fully retracted position. In both embodiments wherein the post 20 is either partially extended for fully retracted when the snare 22 is in the fully retracted position, the suture 26 is bound between the post 20 and the snare 22. With the suture 26 grasped between the post 20 and snare 22 in the fully retracted position, the cannulated needle 14 is pulled out of the tissue, pulling suture through the tissue.

It should be understood that the values used above are only representative values, and other values may be in keeping with the spirit and intention of this disclosure.

While several inventive embodiments have been described and illustrated herein with reference to certain exemplary embodiments, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein (and it will be understood by one skilled in the art that various changes in detail may be effected therein without departing from the spirit and scope of the invention as defined by claims that can be supported by the written description and drawings). More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Further, where exemplary embodiments are described with reference to a certain number of elements it will be understood that the exemplary embodiments can be practiced utilizing either less than or more than the certain number of elements.

All references, including publications, patent applications, and patents, cited herein are hereby incorporated by reference to the same extent as if each reference were individually and specifically indicated to be incorporated by reference and were set forth in its entirety herein.

All definitions, as defined and used herein, should be understood to control over dictionary definitions, definitions in documents incorporated by reference, and/or ordinary meanings of the defined terms.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if not directly attached to where there is something intervening.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

The recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not impose a limitation on the scope of the invention unless otherwise claimed.

No language in the specification should be construed as indicating any non-claimed element as essential to the practice of the invention.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It will be apparent to those skilled in the art that various modifications and variations can be made to the present invention without departing from the spirit and scope of the invention. There is no intention to limit the invention to the specific form or forms disclosed, but on the contrary, the intention is to cover all modifications, alternative constructions, and equivalents falling within the spirit and scope of the invention, as defined in the appended claims. Thus, it is intended that the present invention cover the modifications and variations of this invention provided they come within the scope of the appended claims and their equivalents.

What is claimed is:

1. A suture passer, comprising:
   a cannulated needle having a distal tip having a central longitudinal axis;
   a post slidable within the cannulated needle and extendable outside the cannulated needle to a most extended position;
   a snare slidable within the cannulated needle between the most extended position and a retracted position, wherein the snare is a loop having an opening formed by a first arm, a second arm and a most distal tip portion, wherein each of the first arm and the second arm extends out of the cannulated needle in the most extended position such that the most distal tip portion extends in a direction away from the post, and wherein each of the first arm and the second arm is bent at an angle to the central longitudinal axis in the same direction so that the most distal tip portion extends toward the post and the loop extends around the post in the retracted position; and
   wherein when the snare and the post are in the most extended position, the snare extends from the distal tip of the cannulated needle and the post is not extending through the snare.

2. The suture passer of claim 1, further comprising a handle extending proximally from the cannulated needle.

3. The suture passer of claim 1, further comprising a bent portion in the cannulated needle.

4. The suture passer of claim 3, wherein the distal tip of the cannulated needle extends from the bent portion.

5. The suture passer of claim 3, wherein the bent portion is crescent shaped.

6. The suture passer of claim 3, wherein the bent portion is a 45-degree curve.

7. The suture passer of claim 1, wherein the snare extends at an angle relative to the post in the most extended position.

8. The suture passer of claim 1, wherein the loop of a first size in the most extended position and a second size in the retracted position, the first size larger than the second size.

9. The suture passer of claim 1, wherein the snare is expandable, increasing in size from the retracted position to the most extended position.

10. A suture passer, comprising:
    a proximal handle with a cannulated needle extending distally therefrom, the cannulated needle terminating in a distal tip having a central longitudinal axis;
    a post slidable within the cannulated needle between a most extended position and a retracted position;
    a snare slidable within the cannulated needle between the most extended position and the retracted position, wherein the snare is a loop having an opening formed by a first arm, a second arm and a most distal tip portion, wherein each of the first arm and the second arm extends out of the cannulated needle in the most extended position such that the most distal tip portion extends in a direction away from the post, and wherein each of the first arm and the second arm is bent at an angle to the central longitudinal axis in the same direction so that the most distal tip portion extends toward the post and the loop extends around the post in the retracted position; and
    wherein when the snare and the post are in the most extended position, the snare extends from the distal tip of the cannulated needle and the post is not extending through the snare.

11. The suture passer of claim 10, further comprising an open region between the snare and the post when the snare and the post are in the most extended position.

12. The suture passer of claim 11, wherein the open region is closed, forming a closed region when the snare moves from the most extended position to the retracted position.

13. The suture passer of claim 10, wherein when in the most extended position, the snare extends at an angle relative to the post.

14. A method for passing suture, comprising the steps of:
    providing the suture passer of claim 1;
    passing the distal tip of the cannulated needle through a tissue;
    extending the snare and the post out from the distal tip of the cannulated needle to the most extended position, forming an open region between the snare and the post;
    passing the suture through the open region between the snare and the post; and
    retracting the snare proximally through the cannulated needle to the retracted position, closing the open region around the suture.

15. The method of claim 14, further comprising the step of retracting the post proximally through the cannulated needle to the retracted position.

16. The method of claim 14, further comprising the step of retracting the cannulated needle back through the tissue.

17. The method of claim 14, wherein in the most extended position, the snare extends at an angle relative to the post.

18. The method of claim 14, wherein the cannulated needle comprises a bent portion extending to the distal tip.

19. The method of claim 14, wherein the snare is a loop of a first size in the most extended position and a second size in the retracted position, the first size larger than the second size.

* * * * *